United States Patent [19]

Feuer

[11] 4,226,884
[45] * Oct. 7, 1980

[54] L-GAMMA-GLUTAMYL-TAURINE AS EXTRACTED FROM PARATHYROID GLAND AND METHOD OF TREATMENT USING SAME

[75] Inventor: Laszlo Feuer, Budapest, Hungary

[73] Assignee: Chinoin Gyógyszer és Vegyészeti Termekek Gyára Rt., Budapest, Hungary

[*] Notice: The portion of the term of this patent subsequent to Jan. 4, 1994, has been disclaimed.

[21] Appl. No.: 756,409

[22] Filed: Jan. 3, 1977

Related U.S. Application Data

[63] Continuation-in-part of Ser. No. 457,627, Apr. 3, 1974, Pat. No. 4,001,396, which is a continuation-in-part of Ser. No. 274,723, Jul. 24, 1972, abandoned.

[30] Foreign Application Priority Data

Aug. 4, 1971 [HU] Hungary .................................... 1146

[51] Int. Cl.$^2$ .................. A61K 31/255; C07C 143/12

[52] U.S. Cl. .............................. 424/303; 260/513 N; 424/112

[58] Field of Search ..................... 260/513 N; 424/303

[56] References Cited

U.S. PATENT DOCUMENTS 4,001,396   1/1977   Feuer .................................. 424/112

OTHER PUBLICATIONS

Feuer et al., Chemical Abstract, 84, 126,754(b) (1976), (Abstract from Ger. Offen. 2,517,028, 11/20/75).

*Primary Examiner*—Nicky Chan
*Attorney, Agent, or Firm*—Karl F. Ross

[57] ABSTRACT

A deproteinized, defatted aqueous extract of the parathyroid gland insoluble in benzene, chloroform and carbon tetrachloride is found to be L-gamma-glutamyl-taurine which has vitamin-A type activity and is generally effective for the treatment of a wide range of mammalian disorders which are directly or indirectly connected with pathological alterations of the aerobiospherical genetical adaptational system (AGAS).

2 Claims, No Drawings

L-GAMMA-GLUTAMYL-TAURINE AS EXTRACTED FROM PARATHYROID GLAND AND METHOD OF TREATMENT USING SAME

CROSS-REFERENCE TO RELATED APPLICATIONS

The present application is a continuation-in-part of copending application Ser. No. 457,627 filed Apr. 3, 1974, now U.S. Pat. No. 4,001,396, as a continuation-in-part of Ser. No. 274,723 filed July 24, 1972, now abandoned.

FIELD OF THE INVENTION

My present invention relates to a hormonal substance derived from the parathyroid gland and to a method of treatment using same. The hormonal substance, LITORALON, which has been found to be L-gamma-glutamyl-taurine, has a wide range of therapeutic applications in the treatment of disorders related to pathological alterations of the aerobiospherical genetical adaptational system of mammalia.

BACKGROUND OF THE INVENTION

The literature has described hormones of the parathyroid gland, namely, parathormone having a molecular weight of 8,500, which increases the blood calcium level of the organism.

This hormone is a substance of polypeptide structure and is prepared by extracting ground and degreased parathyroid gland with warm hydrochloric acid or phenol.

OBJECTS OF THE INVENTION

It is an object of the invention to provide a new hormonal substance, also derived from the parathyroid gland, which has utility in a wide range of therapeutic applications in the treatment of disorders related to pathological alterations of the aerobiospherical genetical adaptational system in mammals.

It is another object of the invention to provide a method of treatment of mammalian subjects for a wide range of conditions related to pathological alteration of the aerobiospherical genetical adaptational system.

It is also an object of the invention to provide pharmaceutical and therapeutic compositions incorporating the hormonal substance.

DESCRIPTION OF THE INVENTION

The present invention is based on my surprising discovery that the parathyroid gland contains in addition to the known hormone parathormone, a further compound, namely L-gamma-glutamyl-taurine, with hormonal effect which differs essentially from the substance formerly described and which I have designated as LITORALON in my earlier application.

A. General Description of LITORALON

The chemical structure of the hormonal substance LITORALON has now been made clear and is L-gamma-glutamyl-taurine:

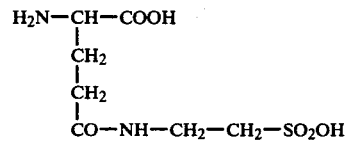

The new hormonal product can be characterized as follows:

It is soluble in water, it is neither a protein nor a steroid; it is a micropeptide-like compound with a molecular weight of 254, it has no fatty character, and it is not soluble in benzene, chloroform and carbon tetrachloride.

The hormonal product possesses the following physiological effects: it exerts a radioprotective effect (i.e. protects organisms against the detrimental effects of alpha, beta and gamma radiation).

The new hormonal substance does not affect the level of calcium in the blood, unlike the known parathyroid hormone, but increases the level of silicon in the blood.

The compound possesses extensive pharmacological and therapeutical effects, as described below, in biologically small concentrations of under 1 $\mu$g/kg of body weight.

The L-gamma-glutamyl-taurine has the following additional chemical characteristics: it is not precipitated with trichloroacetic acid, and is not unambiguously of a protein or polypeptide character. It is soluble in water if advisable part of characterization.

B. Method of Obtention—General

The LITORALON hormone and concentrates or mixtures containing the same, with L-gamma-glutamyl-taurine as the active principle, are prepared by drying and grinding the parathyroid gland of a mammal which may previously be degreased, whereafter it is extracted with water and the solution obtained is lyophilized. Suitable starting materials for the preparation of LITORALON are also the tissue or cellular cultures derived from the parathyroid gland of mammals.

The concentrate thus prepared, in an aqueous solution, or as the lyophilized powder, exhibits the therapeutic or biological effects described.

The purer products and the isolated compound itself are more convenient starting materials for pharmaceutical products for esthetic or precise dosage reasons.

The aqueous extract may be made free from proteins and polypeptides by adding to the extract an agent precipitating the proteins and using the solution obtained after elimination of the precipitating agent.

As protein precipitating agents trichloroacetic acid and sulfosalicyclic acid may be used. Also methods of removing the proteins by adding solvents and by salting them out can be used. The excess of trichloroacetic acid can be removed by a series of extractions with ether.

According to my observations the separation of protein, polypeptide and other fractions can be also carried out with very good results by gel-filtration. In this case the desired substance can be obtained in great purity in the suitable fraction. A very practical method is the purification by gel-filtration after the elimination of proteins in the aqueous fraction. As described with gel-filtration on a column with a great separative capacity, or by a repeated gel-filtration of a small fraction, a LITORALON fraction with a relatively high purity can be obtained.

The purification of the active ingredient can be effected in several ways and for this purpose such methods as extraction, precipitation, absorption etc. and combinations thereof can be used.

As already mentioned, LITORALON has now been fully identified as L-gamma-glutamyl-taurine. The compound may be synthesized as described by me and others in commonly owned copending application Ser. No. 571,766 filed Apr. 25, 1975, now abandoned.

C. Method of Administration—General

The present invention also relates to therapeutic and/or preventive compositions which contain as active ingredient LITORALON (L-gamma-glutamyl-taurine) in admixture with inert, solid or liquid carriers. The active ingredient content of these compositions can vary within wide ranges and is preferably about 0.05–10 mg/dose in human therapy.

These products can be prepared by conventional methods used in the pharmaceutical industry from solid or liquid concentrates containing LITORALON, or from mixtures, in the form of tablets, suppositories, solutions, ointments, powder mixtures or sprays.

Tablets with an active ingredient content of 0.05–5 mg (product of Example III) can be prepared by a wet granulation process, although dry technology is also applicable. Any kind of harmless, inert additives which have hitherto been employed in the pharmaceutical industry can be used to make tablets.

An injectable solution may be prepared from an aqueous solution in a concentration of about 0.05–5 mg/ml, but in this case the above-mentioned removal of proteins is necessary and the perfect removal of the protein-precipitating agents is also required. The more feasible preparation of an injection solution is by the sterile filtration of the aqueous concentrate. The injection solution has no tissue-irritating effect and does not cause any anaphylactic side effects.

Ointments can be prepared from LITORALON having an active ingredient content of 0.01–0.1 mg/g. For this purpose most of the basic hydrophilic and hydrophobic therapeutic ointment materials are suitable. The situation is similar in preparation of suppositories in which cacao butter and the basic synthetic suppository bases (e.g. Witepsol mass) are suitable. The active ingredient (LITORALON) content of the suppositories depends on the purity of the concentrate and should be about 0.05–5 mg.

The present invention is directed also to cosmetic preparations containing LITORALON as an active ingredient. The cosmetic preparations can be prepared from solid or liquid LITORALON concentrates with known solvents after addition of additive-, filling-, diluting-, lubricant- and carrier substances in the form of ointments, solutions, creams, emulsions, powder mixtures, sprays, etc. with a LITORALON concentration of about 0.01–0.5 mg/g.

D. Physiological Effect—General

A wide range of clinical-therapeutical investigations have been carried out with LITORALON as further described in detail. The daily dosage was threefold 0.1–0.5 mg of the LITORALON concentrate orally. Practically no harmful side effect was observed on a patient sample of about 3000 persons. In some cases the appearance of an urticarous eruption on the skin surface was observed, or, from time to time, nausea and a vomiting sensation. These complaints occurred only with 5% of the treated patients and were not considered significant in light of the therapeutic effects achieved.

The following physiological effects are characteristic of the hormonal substance according to the invention:

a. Pharmacological effect of administration of LITORALON

The calcium level in the blood serum is not practically affected. There is an increase of the blood silicon content and modification of the concentration of other essential trace elements, e.g. Zn, Cu, F.

b. Clinical effect of administration of LITORALON

The hormonal product (LITORALON) has been found to be effective in the treatment of human patients for radiation poisoning treatment and prevention.
Protection against radiation:
  Radioprotection
  Therapy of ray injuries
  Metheoropathy
  Cosmonautics.

The pharmacological and chemical tests have been regularly carried out for several years by eight university chairs, national institutes and pharmaceutical factories. The clinical tests were carried out by twenty university clinics, national institutes and hospitals in Budapest over the same period. The therapeutic tests on different clinical indications have reached 3000 persons. The therapeutic effect on some clinical indications appears only after a regular treatment of several weeks or some months; there are nevertheless relatively rapid results too (e.g. ozaena). In some cases the remission is lasting, in other cases it depends on the hormones and the patients rapidly relapse after interruption of the treatment (e.g. rhinopharyngitis sicca).

The L-gamma-glutamyl-taurine manifests its therapeutic effect in a very small concentration (in a concentration of 1/1000 ppm, or below, corresponding to an oral dose of one microgram/kg body weight).

LITORALON differs, however, from cortisone derivatives not only in the significantly different indications (it has in numerous cases the opposite effect), but also in its significantly lower toxicity. Generally it displays a slow, gradually developing improvement contrary to the often prompt results with cortisone and exerts a favorable influence mainly in chronic, degenerative, sclerotizing progressions and not in inflammatory, excoriating and flaring-up states. No significant harmful side effect was observed during a lasting clinical treatment of one year.

SPECIFIC EXAMPLES

EXAMPLE I 10 g of lyophilized and ground parathyroid gland powder derived from cadavers or such slaughterhouse animals as cows, pigs, horses, sheep are degreased in a known manner (Aurbach) as follows:

The gland powder is mixed at room temperature with 25 ml of abs. acetone and then filtered on a glass filter No. G$_4$. The well drained gland powder is again mixed at room temperature with 25 ml of chloroform and filtered on a glass filter No. G$_4$; this operation is repeated. The filtered substance is suspended again in 25 ml of abs. acetone, and sucked on a glass filter No. G$_4$. The obtained gland powder is dried in vacuo at room temperature. The weight of the dry substance obtained varies from 7–9 g, depending on the fat content of the initial substance.

10 g of degreased dry gland powder are extracted with three-fold 100 ml of distilled water at room temperature for 1 hour under a nitrogen atmosphere. Between the extractions the gland powder is separated from the liquid phase by a high speed laboratory centrifuge. The extracted fractions are stored at a temperature of 3°-5° C., in a nitrogen atmosphere until used further. The aqueous extracts are ninhydrin, biuret and trichloro-acetic acid positive.

Thereafter the aqueous extracts are collected and an amount of a 50% volume % trichloroacetic acid is added with constant dropping rate and shaking to a final trichloroacetic acid concentration should be 15%.

After standing for 1 hour at a temperature of 3°-5° C. the trichloroacetic acid precipitate is centrifuged. The upper layer is a clear aqueous solution, which is trichloroacetic acid negative, and ninhydrin positive.

The excess of trichloroacetic acid is removed by serial extractions at room temperature with an aqueous solution of ether (1-1.2 vol. ether: 1 vol. water). For the total removal of the trichloroacetic acid generally 17-18 extractions are necessary; in practice 20-25 extractions are carried out.

After the last extraction the pH of the aqueous phase must have a value of 4.5-5.

The removal of ether lasts 6 hours and is carried out in a nitrogen atmosphere, by means of a water pump at a temperature not exceeding 30° C.

The removal of ether is connected with a decrease of the volume (one part of the aqueous phase is distilled off too).

The total removal of ether is ascertained by smelling.

The aqueous solution is thereafter lyophilized and stored in a well closed vessel (it is hygroscopic).

The yield related to the total amount of initial gland powder (before degreasing) is 10-15%, depending on the fat content.

The lyophilizate of the protein-free aqueous solution contains one unit per milligram (U/mg) of the active principle. The biological determination of the standard unit (U) of LITORALON is given below.

EXAMPLE II

Applying the method described in Example I, an extract from the protein content and of the precipitating agent is prepared from an aqueous extract of degreased parathyroid glands. 5 g of a trichloroacetic acid inactive lyophilizate are gel-filtered on a column containing Sephadex $G_{15}$ (Dextran Polymer, Diethylaminoethyl). Size of the column is 4.3 fold 144 cm. The eluent is water.

Flow speed: 60 ml/hour.
Size of fraction: 15 ml.
Weight of the collected lyophilized samples during fractionation:

| Number of tubes | Weight/mg |
| --- | --- |
| 46-83 | 913 |
| 84-98 | 1126 |
| 99-118 | 999 |
| 119-136 | 1416 |
| 137-154 | 24 |
| 155-170 | 3 |
| 185-198 | 19 |
| 221-230 | 2 |
| 238-265 | 15 |
| 279-285 | 1 |

-continued

| Number of tubes | Weight/mg |
| --- | --- |
| TOTAL: | 4518 mg/90%/ |

The main fraction tube number 46-83, containing 913 mg is rich in LITORALON and possesses in an oral dose of 5-10 micrograms/kg body weight an express physiological and therapeutical activity.

This is the substance containing the first two peaks of the gel-filtration.

The suitable separation of the fraction can be carried out with the following methods of detection:

a. Measuring spectrophotometric absorption at 280 millimicrons.

b. Measuring spectrophotometric absorption at 234 millimicrons.

c. Measuring spectrophotometric absorption at 360 millimicrons.

d. Measuring electric conductivity.

e. A qualitative analysis of chloride ions with silver nitrate.

f. The pH measuring of the fractions belonging to the different peaks.

g. Investigation with ninhydrin reagent.

h. Investigation with the naked eye of the opalescence and color/yellowish/.

The yield of the main fraction 46-83 is 2-2.5% calculated on the dry, not degreased parathyroid powder.

The lyophilizate of the protein-free aqueous solution contains 10 units per milligram (U/mg) of the active principle.

The biological determination of the standard unit (U) of LITORALON is given below.

EXAMPLE III

The process according to Example II is carried out except that the two first peaks are collected in separate main fractions. Thus 302 mg main fraction I, and 555 mg of main fraction II are obtained from 5 g of a protein-free aqueous extract.

Thereafter the main fraction II is gel-filtered again. 456 mg of the substance are carried on the column, water is used as an eluent. The size of the column 4.3 fold is 144 cm; the flowing speed is 50 ml/h. The size of the fraction is 10 ml. Filler: Sephadex $G_{15}$.

Thus the II main fraction can be split into three further peaks. The fractions belonging to the middle peak are united. The weight after lyophilizing is 237.5 mg.

The yield calculated on a dry, not degreased parathyroid gland powder is 0.6-0.8%.

The lyophilizate of the protein-free aqueous solution contains 10 U/mg of the active principle.

The yellow solid is treated with ethanol and a solid is crystallized out with a melting point of 202° to 204° C. This compound has the empirical formula $C_7H_{14}N_2O_6S$. Spectrographic analysis showed it to be L-gamma-glutamyl-tuarine. This compound has a definite physiological and therapeutical effect even in a dose of 1 microgram/kg body weight.

The lyophilized product can be purified by chromatographic and other methods.

By means of a column filled with cellulose or an ion-exchange resin the contaminating amino-acids can be removed (lysine, glutaminic acid, glycine). Thus LITORALON can be obtained, still contaminated, with a yield of 0.3-0.4% calculated on the dry parathyroid gland powder. This product is effective in a concentration below 1 mcg/body weight kg.

EXAMPLE IV

The substance described in Example I is gel-filtered on Sephadex G-15 ("Pharmacia" made in Sweden, particle size 90–120 microns) with descending technology.

The elution diagram is measured at 280 nm extinction. Measuring the volume of the liquid quantity coursed down by the function of the extinction, the second peak from the beginning contains the LITORALON.

The characteristic parameters of gelfiltration are as follows:

Measurement: 5.1 g substance (from Example I) dissolved in 10 ml of water.
Diameter of column: 4.85 cm
Height of column: 149 cm
Flowing velocity: 0.78 ml/minute
Time: 10 minutes

| Fraction size: 7.8 ml/tube | |
|---|---|
| A peak | 77–103 tubes |
| B peak | 104–128 tubes |
| C peak | 129–134 tubes |
| D peak | 135–162 tubes |
| E peak | 163–189 tubes |
| F peak | 190–217 tubes |
| G peak | 218–227 tubes |

The peak B contains the active ingredient.

Elution volume of 104 tubes is 814 ml. The whole volume of peak B is 188 ml.

Between the peaks D and E the chlorine reaction is positive. The dry lyophilized weight of peak B varies between 0.43–0.53 g in case of about 5 g starting material.

The lyophilizate of the protein-free aqueous solution contains 10 U/mg.

Identification by gelfiltration:

After gelfiltration on Sephadex G-15 the substance has to appear in the eluate at $(0.67 \pm 0.02) \times V_o$ if detected by absorption at 280 um in aqueous solution. $V_o$ is the volume at which the salt appears in the eluate. (Positive chlorine reaction.) The peak B is fractionated on a Dowex 50×2 column at pH 1.8.

301 mg substance in 30% aqueous solution is applied on a Dowex 50×2 column of 132×1 cm, which previously was equilibrated with a mixture of formic acid-acetic acid to pH 1.8. Flowing velocity: 13 ml/hour. Size of fraction: 4 ml. The fractions are detected at 280 μm. 9 elution peaks are obtained:

| Sign | Tubes | Weight (mg) | |
|---|---|---|---|
| A | 9–12 | 8.4 | |
| B | 13–17 | 18.4 | |
| C | 18–23 | 64.4 | |
| D | 24–29 | 5.2 | |
| E | 30–36 | 2.2 | |
| F | 37–42 | 0.5 | |
| G | 43–50 | 3.1 | |
| H | 51–57 | 7.3 | |
| I | 58–80 | 6.8 | |
| | | 116.3 | (38.6%) |

The active ingredient can be detected in fractions D, E and F.

The fractions mentioned before are applied to Whatman 3 MM 22 cm broad filter paper and electrophoretized at pH 1.8 and 1500 V for 90 minutes:

The active ingredient is ninhydrine positive and migrates uniformly from the starting line towards the positive pole 5 cm/90 min. at 1500 V.

The product isolated by means of electrophoresis is eluted with water and its biological activity is tested. Yield of the isolated product is 0.01–0.02% calculated on the dry gland powder.

The LITORALON obtained by this way may be considered chemically almost pure and its biological activity was proved by the following tests:

The serumphosphate concentration of rats was significantly decreased by a dosage of 3 gamma/120 g. In the same dosage it decreased significantly the blood sugar. (Dosage: s.c.)

By a dosage of oral tablets of 7 micrograms 3×daily it cured the symptoms of Rhino-laryngo-pharyngitis sicca on man and increased significantly the quantity of AMP discharged with the urine.

EXAMPLE V

After carrying out the process described in Example I the lyophilized end product is subjected to a dialysis. After dissolving 700 mg of the substance in 33 ml of distilled water it is dialyzed in a dialysis-membrane (Kalle 44). Dialysis is carried out against 2 fold 100, and 13 fold 150 ml of distilled water, so that the outer aqueous phase is completely changed in 3.5 hours; in the three nights the aqueous phase must be changed in all 16–16 hours. The dialysis is carried out at a temperature of 5° C.

In the membrane 41 ml of the solution are retained (undialyzed part).

The lyophilized product contains 35 mg of a dried substance.

On evaporating the outer phase at 30° C. in vacuo and lyophilizing 662 mg of a dried substance are obtained.

EXAMPLE VI

Proceeding as described in Example I and starting from 20 g of gland powder (lyophilized and not degreased) the aqueous solution freed from protein and ether is evaporated in vacuo to one-third of its volume, whereupon it is admixed three times with a 1:1 (volume) of chloroform. The aqueous layer is freed from chloroform under nitrogen in vacuo. The chloroform-free aqueous solution is further evaporated in vacuo to a volume of 20 ml and a five-fold amount of acetone is added. The solution is allowed to stand on ice overnight. From the nearly colorless acetonic phase a yellow colored oily part is separated. The acetonic solution is decanted and the yellow oily substance is dried in vacuo until its weight is constant. 1.1 g of a resinous concentrate is obtained (A).

The decanted acetonic solution is evaporated to dryness in vacuo. 1 g of a resinous concentrate is obtained (B).

EXAMPLE VII 50 g of a lyophilized gland powder are degreased as described in Example I. 38 g of a degreased gland powder are obtained which are admixed with 400 ml of a 10% urea solution, after standing for 1 hour it is added to 400 ml of glacial acetic acid and 400 ml of acetone. The mixture is allowed to stand for 1 hour and then a further amount of 1200 ml of acetone and 11.2 ml of a N sodium hydroxide solution are added, it is allowed to precipitate, and filtered through a layer of gauze. 2 lit. of ether are added to the aqueous, urea containing acetonic solution, which is then allowed to stand overnight and decanted. The suspension is centrifuged, twice washed with 50 ml of a 1:1 acetone-ether mixture each. The precipitate obtained is admixed with 200 ml of a 10% acetic acid solution and dissolved. From the solution a precipitate is obtained by adding 10 g of sodium chloride. The precipitate is dissolved in 50 ml of water. It is dialyzed 6 times with 2 liters of water each; the exhausted dializying water is decanted and the residue lyophilized. 732 g of a solid concentrate are obtained (substance C). The substance retained in the solution (197 ml) after precipitating with sodium chloride and centrifuging is treated with 40 ml of 45% trichloroacetic acid and centrifuged. The upper layer is then dialyzed 4 times with 3 lit. of water each, evaporated in vacuo and lyophilized. 86 g of a concentrate are obtained (substance D).

BIOLOGICAL DETERMINATION OF LITORALON

A. Radiation protecting effect of LITORALON

1. Method

Super Lilliput (Medicor, Budapest) X-ray apparatus of 180 kV tube voltage was used. Non-narcotized animals were irradiated by 7.8 R/min dose-output, at 4 mA, through a filter of 0.5 mmCu, at 50 cm focal distance. The male CFE rats (bodyweights ranging from 150 to 250 g) kept in separate plastic cages received X-ray in a dose of 850 R.

Under the effect of LITORALON concentrations the survival time of irradiated rats is increased.

Rats were covered by buckler made of lead, and to the skin of their back, to a circle-shaped field of 1 cm radius 700+500+500, i.e. total 1700 R were given, in three parts.

Under the effect of LITORALON significant reduction in irradiation hyperaemia is noted and earlier pigmentation can be experienced.

2. Experimental Population:

Three groups of 10 rats were used to examine both the survival times and the reduction of X-ray induced erythema.

First group: Control. Animals are exposed to irradiation as described earlier. Two days prior to and two days following irradiation they are given i.p. 1 ml physiological saline, daily.

Second group: The experimental animals receive the same X-ray dose, but instead of physiological saline they are given the LITORALON concentrate of unknown quantity, dissolved in 1 ml of water. Administration is also intraperitoneal. Injections are given on the day of irradiation and throughout the 3 successive days.

Third group: X-ray dose is the same as in the first group but, instead of physiological saline the animals are injected for 4 days before irradiation 1 ml aqueous solution of 0.1 mg AET (2-amino-ethylisothyuronium-bromide-hydrobromide), daily. Administration is intraperitoneal.

Survival time is determined during a 21 day period of observation. The times of death are fixed within the 21 day interval.

The determination of skin erythema is by means of one week observation. The appearance of hyperaemia, its intensity, and the beginning of pigmentation are registered.

3. Evaluation:

One unit of LITORALON is that amount of the active agent which, by using the described experimental method and set up effectuates a 50% (mean value) increase in the survival of rats until the 21st day, e.g. while in the control group the number of surviving animals is 4, in the treated group it amounts to 6.

Considering that in the above experimental set up the effect of LITORALON is the same as that of AET, one of the best known, most effective radioprotective agents, we can also say that one unit of LITORALON represents that amount of the active agent which corresponds to the effect of a 4 day pretreatment with AET, given in daily doses of 0.1 mg/rat, i.p. as described earlier.

Three days after the performance of the skin erythema test, the control group displays strong hyperaemia of the irradiated area and pigmentation of medium degree occurs by the 5th day.

Animals treated with LITORALON concentrate and AET, respectively, manifest significantly milder hyperaemia, compared to the controls and the pigmentation of the skin appears already on the 3rd day. One unit of LITORALON is that amount of the concentrate which exerts the same mitigating effect on skin erythema as 0.1 mg AET administered, i.p.

4. Remarks:

The radioprotective action of LITORALON is in good accordance with clinical findings. Erythema usually occurring in irradiated patients is significantly milder when LITORALON is administered orally, pigmentation of the skin begins sooner. Slight injuries of the mucous membrane can be prevented by LITORALON, e.g. the tormenting desiccation of the mucosa and racking fits of cough lasting for weeks following irradiation of the neck fail to occur after pretreatment with the drug. Promising experience has been obtained in the therapy of torpid skin ulcerations occurring after irradiation with extremely high therapeutic doses.

B. Incorporation of S-35 in chick embryos

1. Method:

Fifteen-day-old chick embryos were injected intraocularly with 0.05 ml sodium sulphate of 10 $\mu$C activity and 0.05 ml of LITORALON concentrate with an unknown amount of active agent.

For 24 hours following injection the eggs (containing embryos) were incubated at 37° C. Further biological processes were arrested by deep freezing to −40° C. and crystalline lenses were removed.

The crystalline lenses were homogenized in distilled water. The aliquot part was treated with trichloroacetic acid (TCA) (0.5 N end concentration) for 10 min. at 4° C. and afterward centrifuged. Radioactivity of the homogenate, supernatant and sediment was measured.

Radioactivity measured in the homogenate represents the total S-35 incorporation in the crystalline lenses, while activity of the supernatant treated with TCA indicate the S-35 content of the so-called acid soluble fraction. Radioactivity of the sediment represents that of the acid insoluble fraction.

2. Experimental Population:

For each biological titration 6 times 12 chick embryos were used.

| I. | group-control | |
|---|---|---|
| II. | group-10 | mg/ml of LITORALON extract (unknown) |
| III. | group-1 | mg/ml of LITORALON extract (unknown) |

-continued

| IV. | group 0.1 | mg/ml of LITORALON extract (unknown) |
| V. | group-0.01 | mg/ml of LITORALON extract (unknown) |
| VI. | group-0.001 | mg/ml of LITORALON extract (unknown) |

In addition, each group was given introaocularly 0.15 ml aqueous solution of sodium-sulphate S-35 in a concentration of 100 μC/ml and except the control, groups from II to VI received 0.05 ml of the solution containing the active agent.

1 LITORALON unit is that amount of the active agent which, by means of the above experimental method and set up, is able to evoke a mean increase of 25% of the sulphate content in the acid soluble fraction of the crystalline lenses (Scattering ±20%, compared to the grade of increase).

3. Remarks:

The increased incorporation of acid soluble sulphate is due to the enhanced formation of sulphomucopolysaccharides.

The logarithm of LITORALON concentration has a definite ratio to the acid soluble sulphate concentration in a certain concentration range, e.g.: In case of fraction P, the sulphate content of acid soluble fraction is doubled when 100 μg of the substance are injected instead of 10 μg. (Fraction P is a LITORALON concentrate obtained by the following procedure: Parathyroid gland is extracted by water, from the aqueous solution proteins are precipitated by trichloroacetic acid, and following gelfiltration the active fraction is freeze-dried.)

It should be mentioned that, in case of higher doses (above 200 μg) the values are decreasing again. Logarithmic values of active concentrate plotted against sulphate content of acid soluble fraction yield a curve with a maximum (at +40%). Therefore with substances of unknown LITORALON concentration it is advisable to examine the curve in the total concentration range and, determine the point of the ascending curve, where the increase of potency is 25% (six experimental groups).

The determination is based on one of the fundamental features of LITORALON hormone, namely, its intervention with the regulation of glyco-mucoproteide balance. This is the basis of some of its therapeutic effects (angiopathies, increase or regulation of mucin secretion, arthroses, spondylosis ankylopoetica, certain diseases of the skin, paradontosis, etc.).

This effect is based on the recognition that the parathyroid produces two trophormones. One of them, the parathormone, transforms vitamin $D_3$ in the liver and kidney to 1.25-cholecalciferol, i.e. to active hormone, in a way well known in literature. The hitherto unknown LITORALON, however, appears to transform vitamin $A_1$ to hormone, presumably also in the liver and kidney. In this way, the two vitamins $D_3$ and $A_1$ having fundamental importance in aquatic life presumably were transformed to prohormones at the beginning of terrestrial life (appearance of amphibia and reptilia in the course of evolution). The transformation of both vitamins into hormones is regulated by the parathyroids.

As is known, vitamin $A_1$ regulates the synthesis of sulphomucopolysaccharides almost in the same way as LITORALON does. (Logarithmic and maximum curve correlations.)

4. References:

See: H. F. de Luca: Parathyroid hormone as a trophic hormone for 1.25 dihydroxyvitamin $D_3$, the metabolically active form of vitamin D. In: New Engl. J. of Med. 287: 250, 1972 and the following articles dealing with sulphate incorporation of vitamin A:

Subka Rao, K., Sechadri Sastry, P., Ganguly, J. Biochem. J. 87: 312, 1963.

Carroll, J., Spencer, B.: Biochem. J. 96: 79 P, 1963.

Fell, H. B., Mellanby, E.: J. Physiol. London, 116: 320, 1952.

Fell, H. B., Mellanby, E., Pelc, S. R.: J. Physiol. London, 134: 179, 1956.

Fell, H. B., Mellanby, E.: J. Physiol. London, 119: 470, 1953.

Fell, H. B., Mellanby, E., Pelc, S. R.: Brit. Med. J. 2: 611, 1954.

Wolf, G., Varandani, P. T.: Biochem. Biophys. Acta, 43: 501, 1960.

Other biological and pharmacological effects were also suitable for determining the biological potency and unit of LITORALON, e.g. its effect on the regulation of trace elements is also characteristic (Si, Cu, Zn, etc.). The detection of these effects, however, is not only complicated but places great demand on instruments and facilities such as atom absorption, neutron-activation analysis. Anyhow, the increase of blood silicon (50-120% in rats and rabbits) is extremely characteristic of the effect of a 2-week treatment with LITORALON as compared to the controls.

NOTE: 1 unit of LITORALON activity corresponds to 0.1 microgram of L-gamma glutamyl taurine.

I claim:

1. L-gamma-glutamyl-taurine.

2. A pharmaceutical composition for the treatment or prevention of radiation poisoning, comprising an effective amount of the compound defined in claim 1 in admixture with a pharmaceutically acceptable carrier.

* * * * *